United States Patent
Yen et al.

(10) Patent No.: US 9,224,955 B1
(45) Date of Patent: Dec. 29, 2015

(54) PURIFYING METHOD FOR ORGANIC OPTOELECTRONIC MATERIAL

(71) Applicants: Feng-Wen Yen, Taipei (TW); Cheng-Hao Chang, Miao-Li (TW)

(72) Inventors: Feng-Wen Yen, Taipei (TW); Cheng-Hao Chang, Miao-Li (TW)

( * ) Notice: Subject to any disclaimer, the term of this patent is extended or adjusted under 35 U.S.C. 154(b) by 0 days.

(21) Appl. No.: 14/529,183

(22) Filed: Oct. 31, 2014

(51) Int. Cl.
  H01L 21/00 (2006.01)
  H01L 21/84 (2006.01)
  H01L 51/00 (2006.01)
  H01L 51/56 (2006.01)
  H01L 51/42 (2006.01)

(52) U.S. Cl.
  CPC ............ *H01L 51/0025* (2013.01); *H01L 51/42* (2013.01); *H01L 51/56* (2013.01)

(58) Field of Classification Search
  CPC .................... H01L 21/0231; H01L 21/02527; H01L 21/0257; H01L 21/265; H01L 25/167; H01L 27/3248; H01L 29/6609; H01L 28/65; H01L 27/14643; H01L 51/5296; H01L 51/5287; H01L 51/5012; H01L 51/0508
  USPC ......... 438/99, 82, 70, 30, 141, 149, 369, 509, 438/510; 257/E21.005, E21.05, E21.051, 257/E21.053, E21.141, E21.152, E21.154, 257/E21.347, E21.352, E21.366, E21.411
  See application file for complete search history.

(56) References Cited

U.S. PATENT DOCUMENTS

| | | | |
|---|---|---|---|
| 6,506,756 B2 * | 1/2003 | Shih ..................... | C07D 401/14 514/253.03 |
| 7,485,691 B1 * | 2/2009 | Guo ....................... | C07F 7/0896 528/17 |
| 7,754,347 B2 * | 7/2010 | Ise .......................... | C09K 11/06 257/E51.044 |
| 2014/0371461 A1 * | 12/2014 | Nakayama ........... | C07D 401/14 546/159 |

* cited by examiner

*Primary Examiner* — David Nhu

(57) ABSTRACT

The present invention discloses a novel purifying method for the organic optoelectronic material. More specifically the present invention relates to a purifying method for organic electroluminescent (herein referred to as organic EL) material, organic photovoltaics (herein referred to as OPV) material and organic thin-film transistor (herein referred to as OTFT) material. The organic optoelectronic device use the organic optoelectronic material can lower driving voltage, prolong half-lifetime and improve performance.

10 Claims, 7 Drawing Sheets

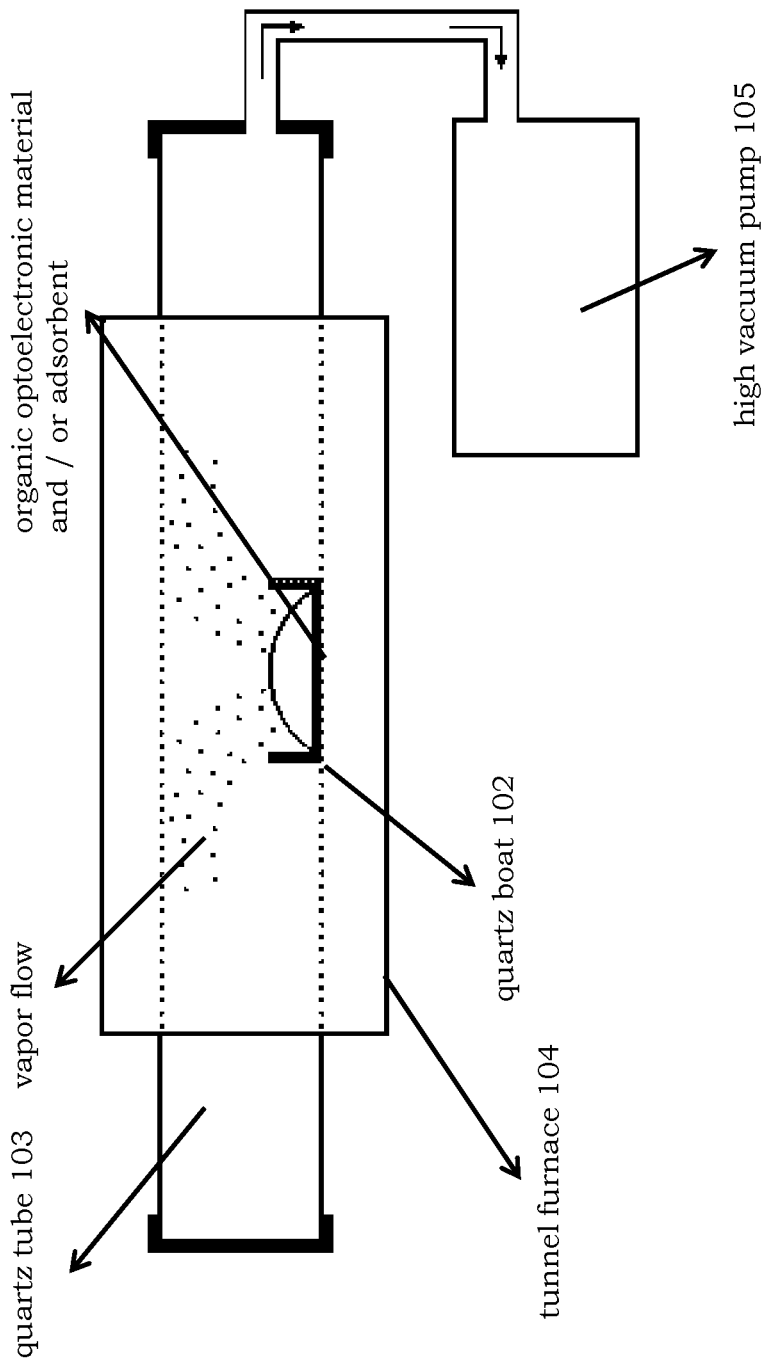
Fig. 1-a  Sublimation equipment

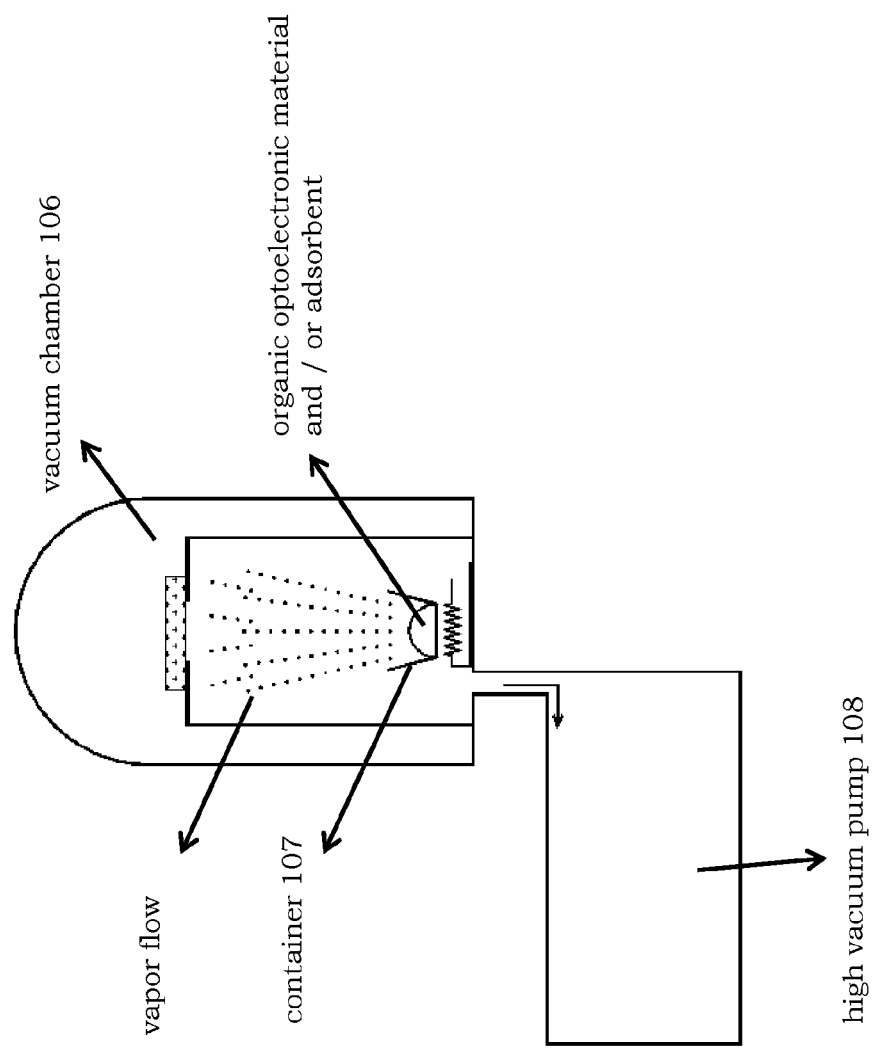
Fig. 1-b  Deposition equipment

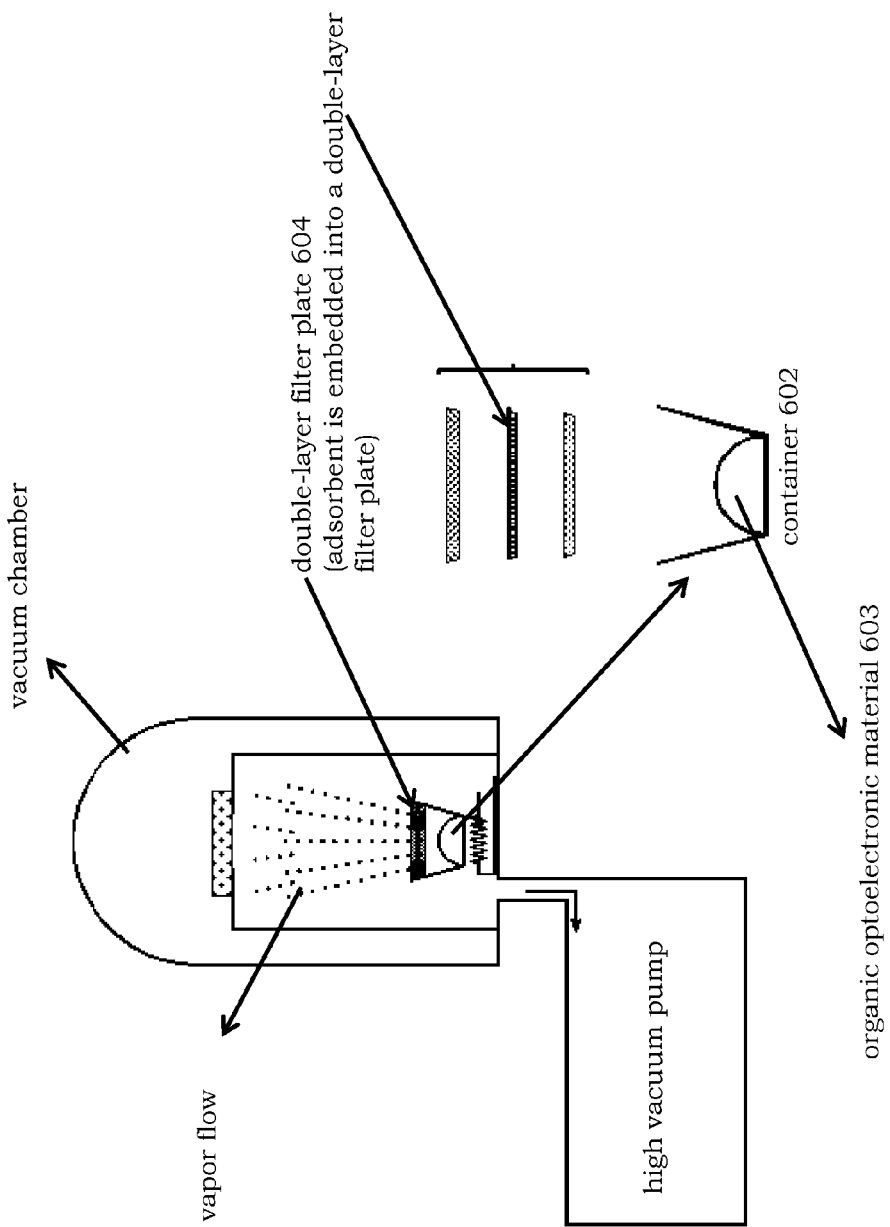

PURIFYING METHOD FOR ORGANIC OPTOELECTRONIC MATERIAL

FIELD OF INVENTION

The present invention generally relates to a novel purifying method for organic optoelectronic material. More specifically the present invention relates to a purifying method for organic electroluminescent (herein referred to as organic EL) material, organic photovoltaics (herein referred to as OPV) material and organic thin-film transistor (herein referred to as OTFT) material. The organic optoelectronic device use the organic optoelectronic material can improve performance.

BACKGROUND OF THE INVENTION

Organic optoelectronic material has been developed for several decades. Recently the organic optoelectronic material are widely put in use in organic optoelectronic devices, such as organic EL device, OPV device and OTFT device have attracted significant attention for industries practice use due to their potential application for flat-panel and flexible display, solid-state lighting, solar energy storage, etc. Organic EL device have many advantages such as self-emitting, wider viewing angles, faster response speeds and highly luminescence. Their simpler fabrication and capable of giving clear display comparable with LCD, making organic EL device an industry display of choice and has stepped into commercialization. OPV has been considered as a highly growing trend for green energy technology because of its low cost, simple preparation and large area capability. The conversion efficiency of OPV had reached to the practical application. OTFT has grown into a hotspot in organic electronics as it also possesses the merits of low cost, flexibility, low temperature processing and large area capability. And its performance is already comparable to that of the amorphous silicon based thin film transistors.

However, there are still many technical problems remaining to be solved in organic optoelectronic devices, such as material impurity, material instability, low power efficiency, short life time, etc., which hindered the commercialization of organic optoelectronic devices. Especially the purity of organic optoelectronic materials need to be improved. Some metal ions, halide ions, dyes, pigments, chromatophores and other residues will appear and dying the organic optoelectronic material during synthesis procedure. These impurities exert an influence to characteristic of organic optoelectronic devices like lower efficiency, shorter half-life time and raise applied driving voltage. Therefore the purifying method for organic optoelectronic material becomes critical technology to organic optoelectronic devices. After finishing organic synthesis procedures, there are some purifying methods to improve the purity like crystallization, recrystallization, column chromatograph, sublimation, etc. Due to many organic optoelectronic materials could not be dissolved in organic solvent, chemical purifying method could not effectual purify these organic optoelectronic materials. Sublimation methods are suitable to purify non-dissolved organic optoelectronic materials. But some metal ions, halide ions, dying colour, pigments, chromatophores, etc., which still involved in organic optoelectronic materials always be bring out via sublimation vapor. These impurities could not be effectual eliminated via sublimation process and also will be bring out during deposition process when fabricate the organic optoelectronic device. The purifying method of sublimation process and deposition process need to be improved for organic optoelectronic material for industrial practice use.

In the present invention, for the purpose to improve the purity of organic optoelectronic material we embedded decolorized material or deionized material (herein referred to as adsorbent) into sublimation process or deposition process to eliminate these impurities. These impurities including metal ions, halide ions, dying colour, pigments, chromatophores, etc., which are absorbed and eliminated when sublimation vapor or deposition vapor passed through the adsorbent to get high purity of organic optoelectronic material.

SUMMARY OF THE INVENTION

In accordance with the present invention, a purifying method for organic optoelectronic material and their use for organic optoelectronic device are provided. The purifying method can eliminate impurities like as metal ions, halide ions, dying colour, pigments, chromatophores, etc. during sublimation process or deposition process. The purifying method for organic optoelectronic material can prolong half-life time, lower driving voltage and power consumption for organic optoelectronic device.

An object of the present invention is to provide a purifying method to eliminate impurities, then produce high purity of organic optoelectronic material.

Another object of the present invention is to apply the high purified organic optoelectronic material to prolong half-life time, lower driving voltage and power consumption for organic optoelectronic (Organic EL, OPV, OTFT) device.

The present invention has the economic advantages for industrial practice. Accordingly, the present invention discloses a purifying method for organic optoelectronic material is disclosed as following:

1. Adsorbent is mixed with organic optoelectronic material and put the mixed material on a quartz boat, then is placed into a quartz tube for sublimation process (See FIG. 2).
2. Adsorbent is embedded into a double-layer filter plate and cover upon a an quartz boat wherein organic optoelectronic material is loaded in, then the quartz boat is placed into a quartz tube for sublimation process (See FIG. 3).
3. Adsorbent is embedded into a double-layer filter cartridges and place on two side of an small quartz tube wherein organic optoelectronic material is loaded in, then the small quartz tube is placed into a quartz tube for sublimation process (See FIG. 4).
4. Adsorbent is mixed with organic optoelectronic material and put the mixed material into a container, then is placed on a heat source of deposition machine for deposition process (See FIG. 5).
5. Adsorbent is embedded into a double-layer filter plate and cover upon a container wherein organic optoelectronic material is loaded in, then is placed on a heat source of deposition machine for deposition process (See FIG. 6). Wherein the adsorbent are selected from active carbon, celite, silica gel, zeolite, activated alumina, carbon molecular sieves, molecular sieves, etc.

The organic optoelectronic material is consisting of Organic EL material, OPV material, OTFT material which are used in organic optoelectronic device. The weight ratio of the adsorbent and the organic optoelectronic material is selected from 1:100 to 100:1.

BRIEF DESCRIPTION OF THE DRAWING

FIG. 1-a show the diagram of sublimation process for equipment including a quartz boat 102 which is used for loading organic optoelectronic material and/or adsorbent, a quartz tube 103 which is used for embedding the quartz boat 102 and collect sublimed product, a tunnel furnace 104 which is used for heating the quartz tube 103 and keep it on an equilibrium temperature and a high vacuum pump 105, which can keep this system under $10^{-6}$ Torr, and this sublimation equipment can sublime organic optoelectronic material. FIG. 1-b show the diagram of deposition equipment including vacuum chamber 106, a container 107 which is used for loading organic optoelectronic material and/or adsorbent, and a high vacuum pump 108, which can keep this system under $10^{-7}$ Torr, and this deposition equipment can evaporate organic optoelectronic material.

FIG. 6 show the diagram of a container 602 which loading the mixed including different weight ratio of the adsorbent and the organic optoelectronic material 603, then a double-layer filter plate 604 which cover upon the container 602.

DESCRIPTION OF THE PREFERRED EMBODIMENTS

What probed into the invention is a purifying method for organic optoelectronic material. Detailed descriptions of the purifying method, equipment, procedures and organic optoelectronic material will be provided in the following to make the invention thoroughly understood. Obviously, the application of the invention is not confined to specific details familiar to those who are skilled in the art. On the other hand, the common purifying method and procedures that are known to everyone are not described in details to avoid unnecessary limits of the invention. Some preferred organic optoelectronic material can be purified by the purifying method of the present invention will now be described in greater detail in the following. However, it should be recognized that the present invention can be practiced in a wide range of other organic optoelectronic materials besides those explicitly described, that is, this invention can also be applied extensively to other organic optoelectronic materials and the scope of the present invention is expressly not limited except as specified in the accompanying claims.

DEFINITION

Figure 2:
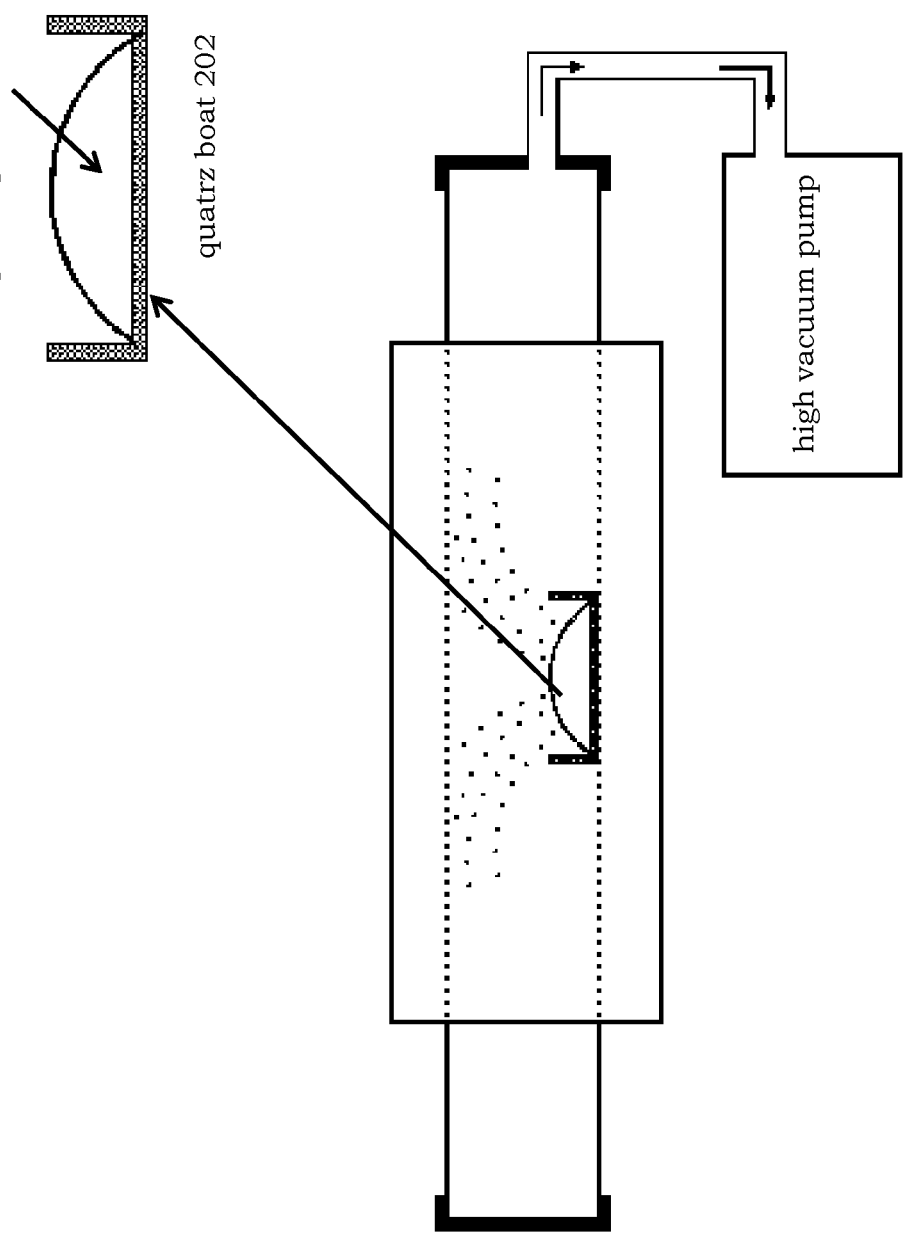
FIG. 2 show the diagram of a quartz boat 202 which loading the mixed material 203 including different weight ratio of the adsorbent and the organic optoelectronic material.

In a first embodiment of the present invention, the present invention discloses a purifying method for organic optoelectronic material is disclosed as following:

1. Adsorbent is mixed with organic optoelectronic material and put the mixed material on a quartz boat, then is placed into a quartz tube for sublimation process (See FIG. 2).

Figure 3:
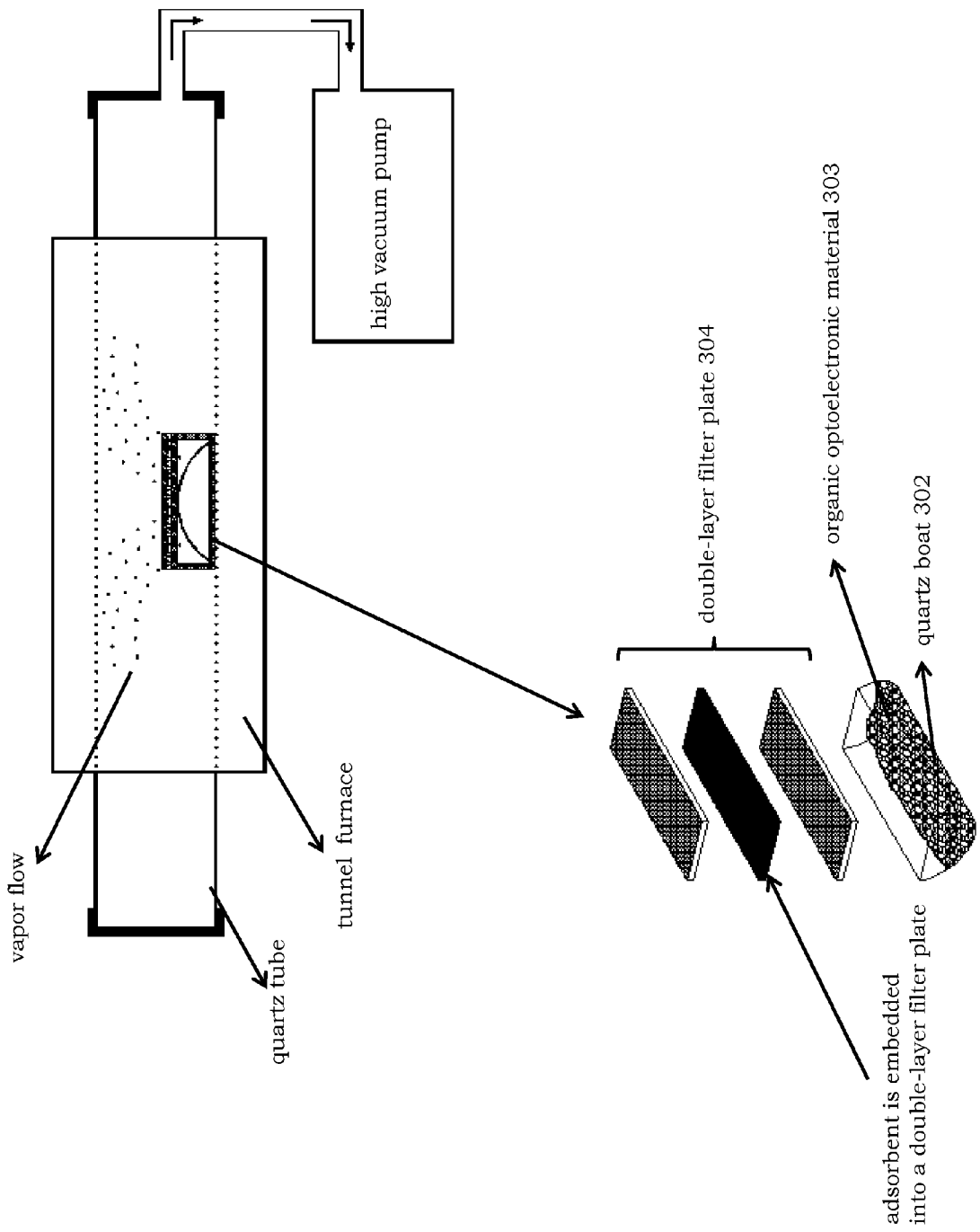
FIG. 3 show the diagram of a quartz boat 302 which loading the organic optoelectronic material 303, then a double-layer filter plate 304 which cover upon the quartz boat 302.

2. Adsorbent is embedded into a double-layer filter plate and cover upon a quartz boat wherein organic optoelectronic material is loaded in, then the quartz boat is placed into a quartz tube for sublimation process (See FIG. 3).

Figure 4:
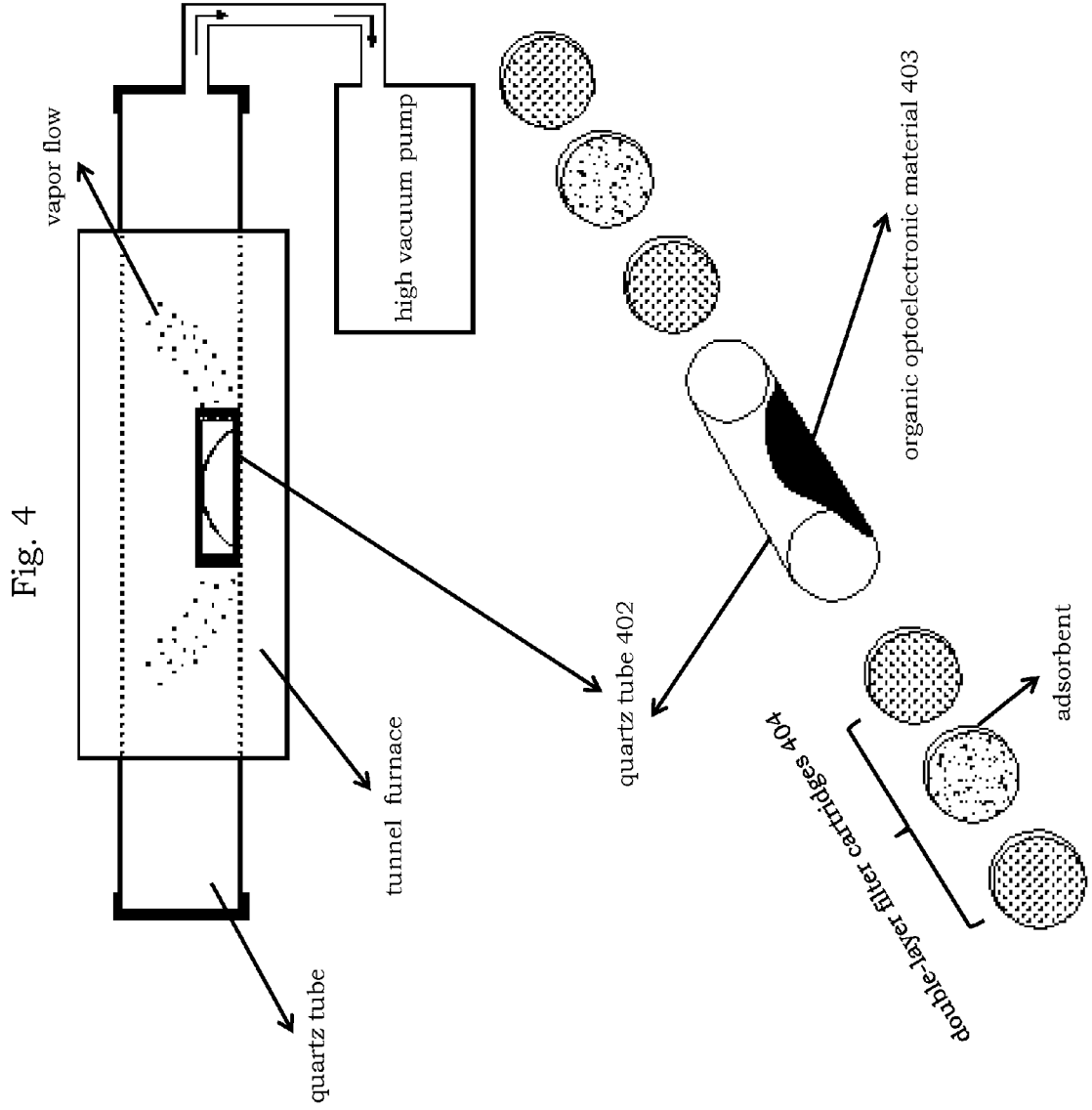
FIG. 4 show the diagram of a quartz tube 402 which loading the organic optoelectronic material 403, then a double-layer filter cartridges 404 which place on two side of the quartz tube 402.

3. Adsorbent is embedded into a double-layer filter cartridges and place on two side of an small quartz tube wherein organic optoelectronic material is loaded in, then the small quartz tube is placed into a quartz tube for sublimation process (See FIG. 4).

Figure 5:
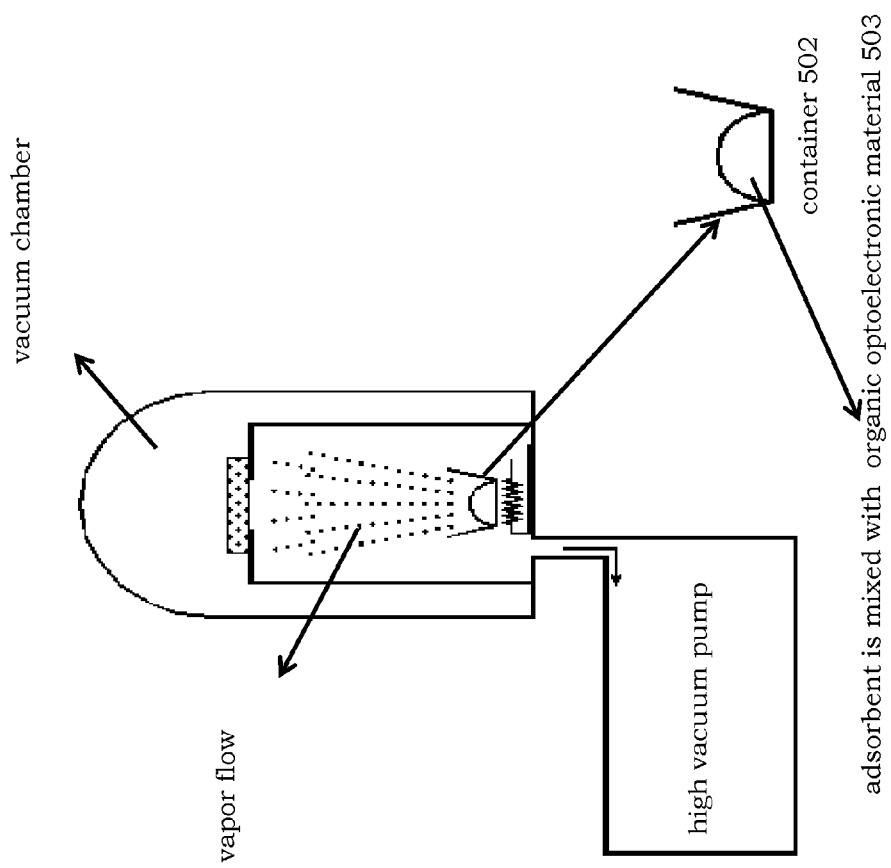
FIG. 5 show the diagram of a container 502 which loading the mixed material 503 including different weight ratio of the adsorbent and the organic optoelectronic material.

4. Adsorbent is mixed with organic optoelectronic material and put the mixed material into a container, then is placed on a heat source of deposition machine for deposition process (See FIG. 5).

5. Adsorbent is embedded into a double-layer filter plate and cover upon a container wherein organic optoelectronic material is loaded in, then is placed on a heat source of deposition machine for deposition process (See FIG. 6). Wherein the adsorbent are selected from active carbon, celite, silica gel, zeolite, activated alumina, carbon molecular sieves, molecular sieves, etc.

The organic optoelectronic material is consisting of Organic EL material, OPV material, OTFT material which are used in organic optoelectronic device. The weight ratio of the adsorbent and the organic optoelectronic material is selected from 1:100 to 100:1.

Some examples of organic optoelectronic material use the purifying method of the present invention are listed as following:

Organic Electroluminescent Material

Hole Transport Layer (HTL) Materials

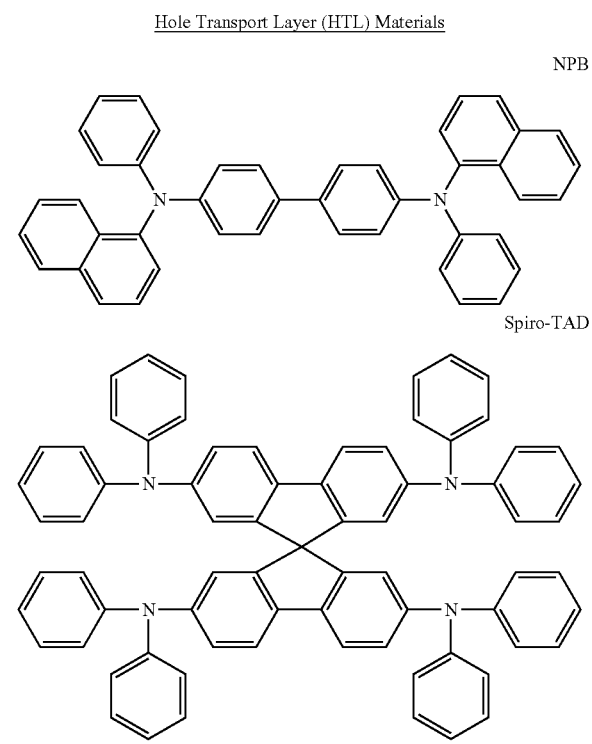

NPB

Spiro-TAD

Spiro-2NPB
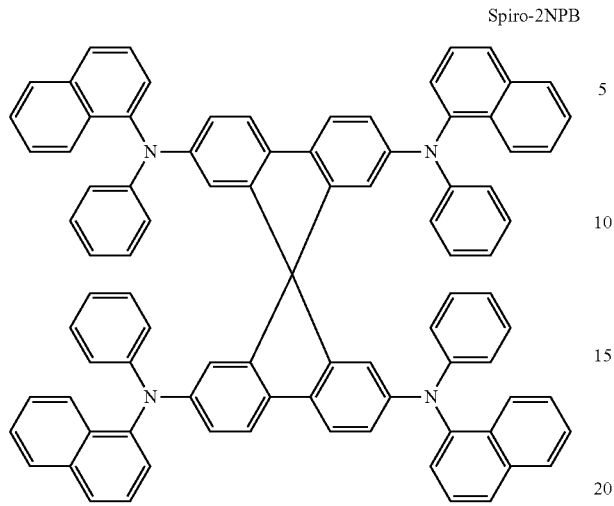
BPAPF
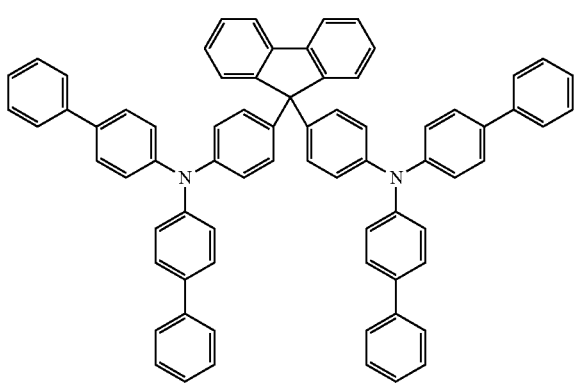
PAPB
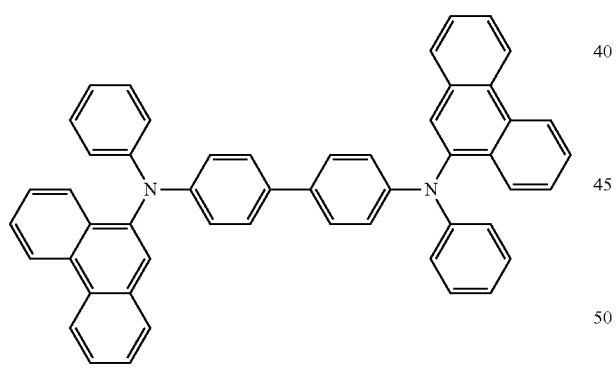
TAPC
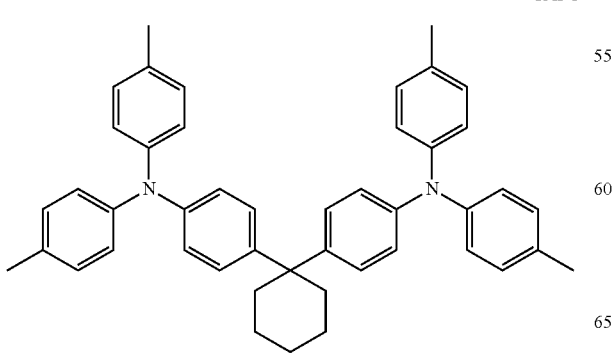
TNB
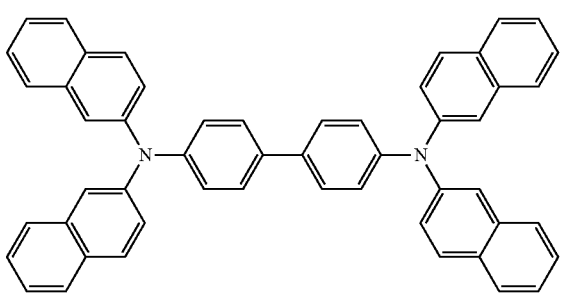
3DTAPBP
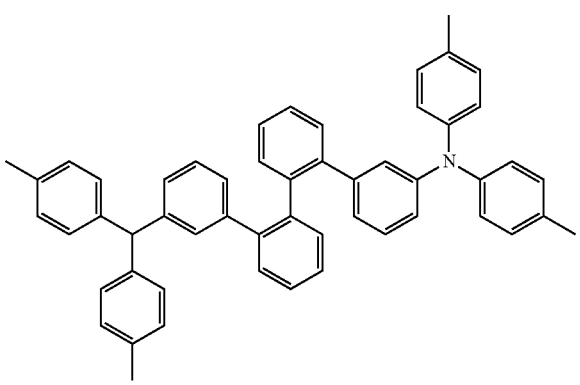
DBTPB
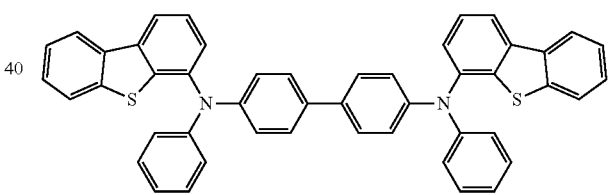
Tris-PCz
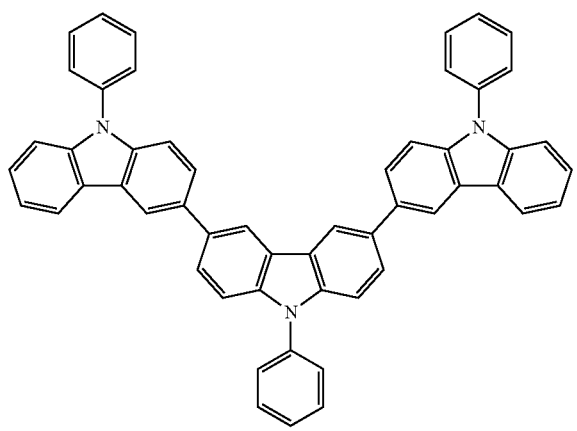

Hole Injection Layer (HIL) Materials
CuPC
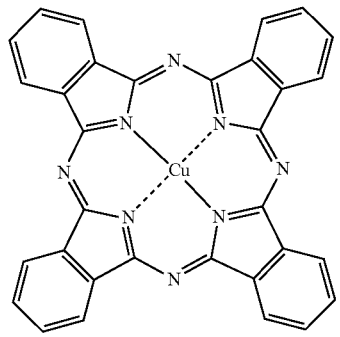
TiOPC
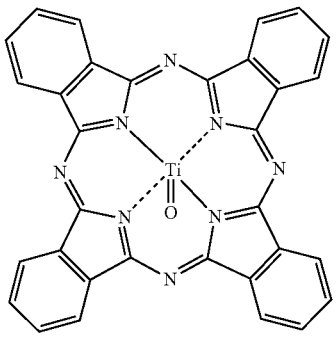
NTNPB
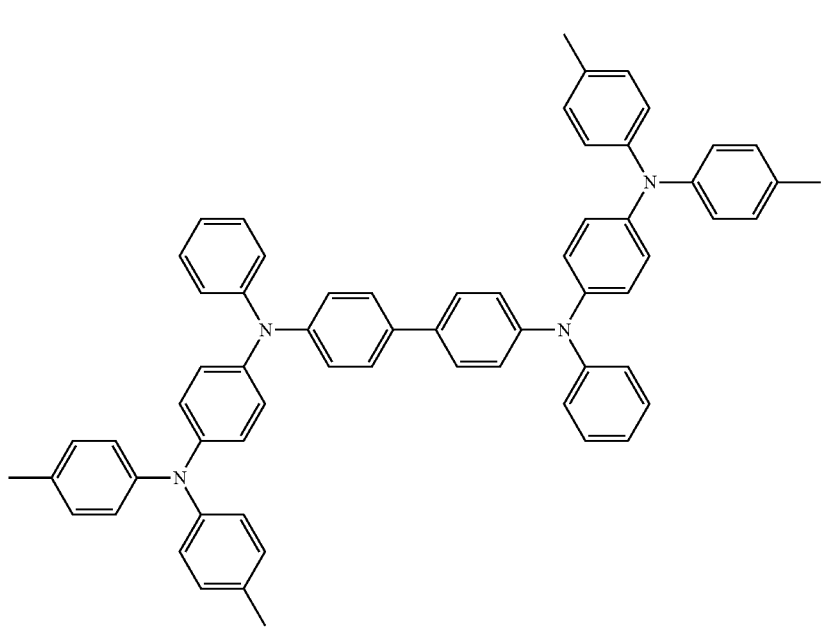
TPTI
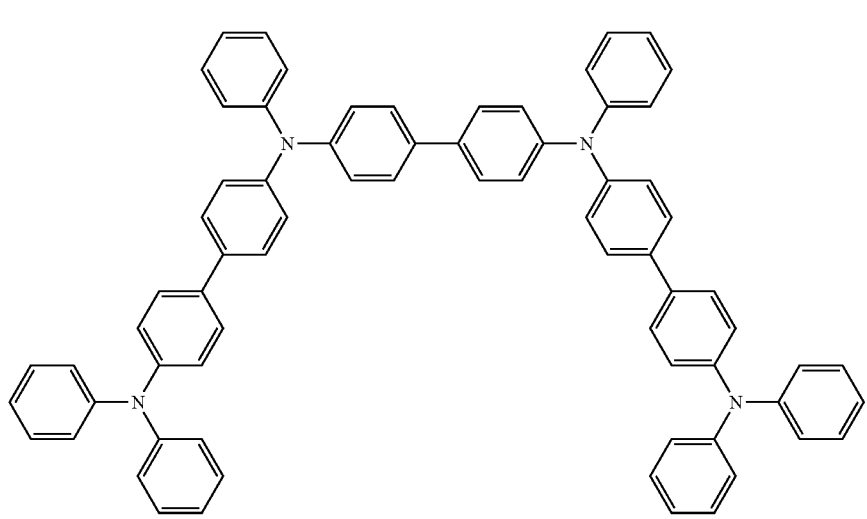

Di-NPB
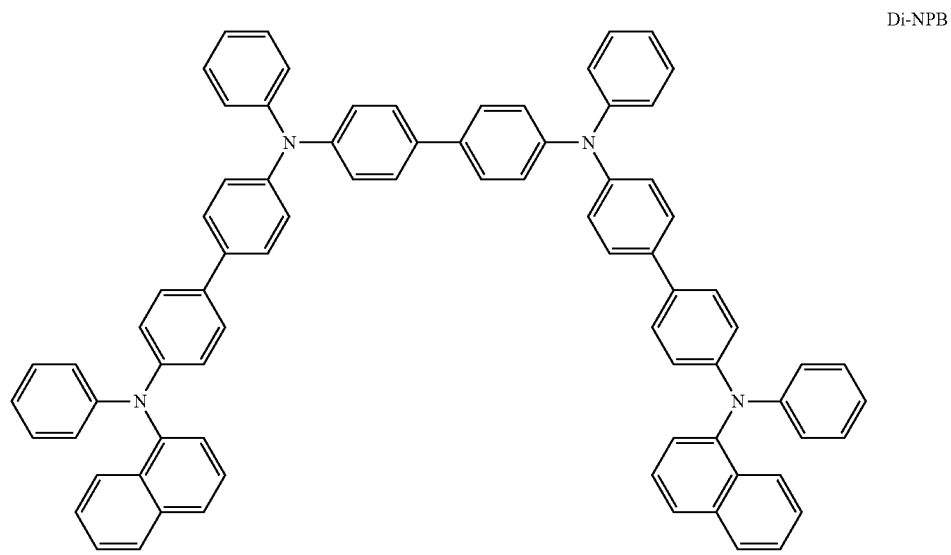
Spiro-MeOTAD  HAT-CN
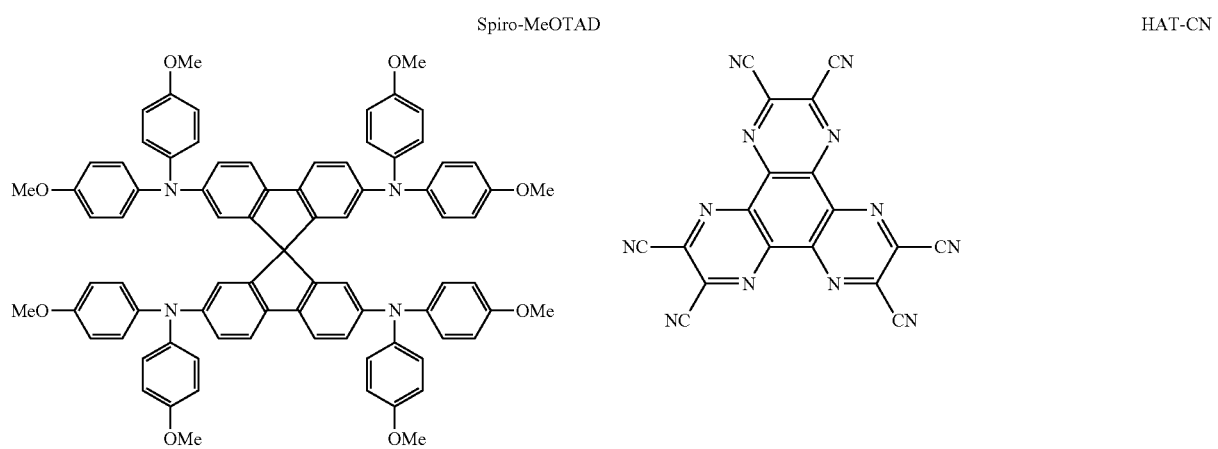
DNTPD
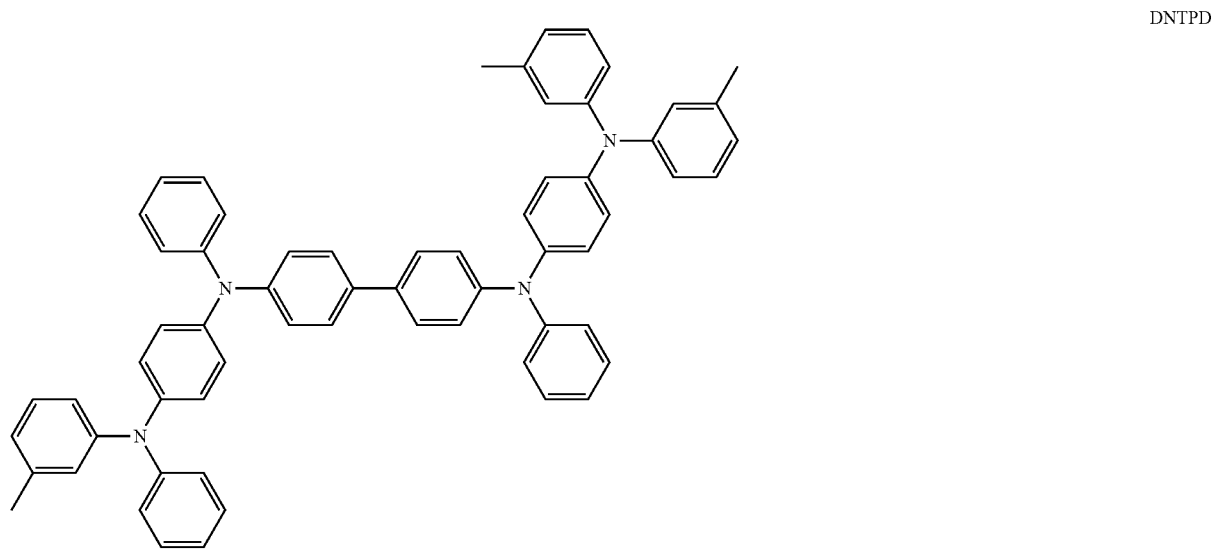

P-type dopant materials
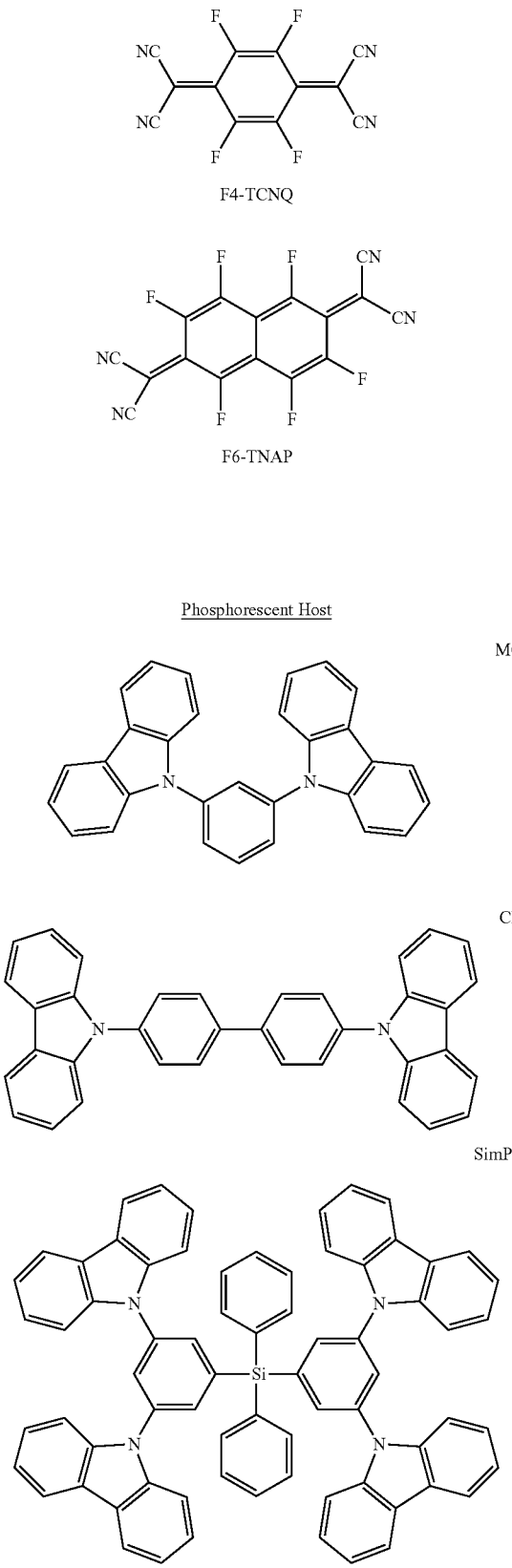
Phosphorescent Host
-continued
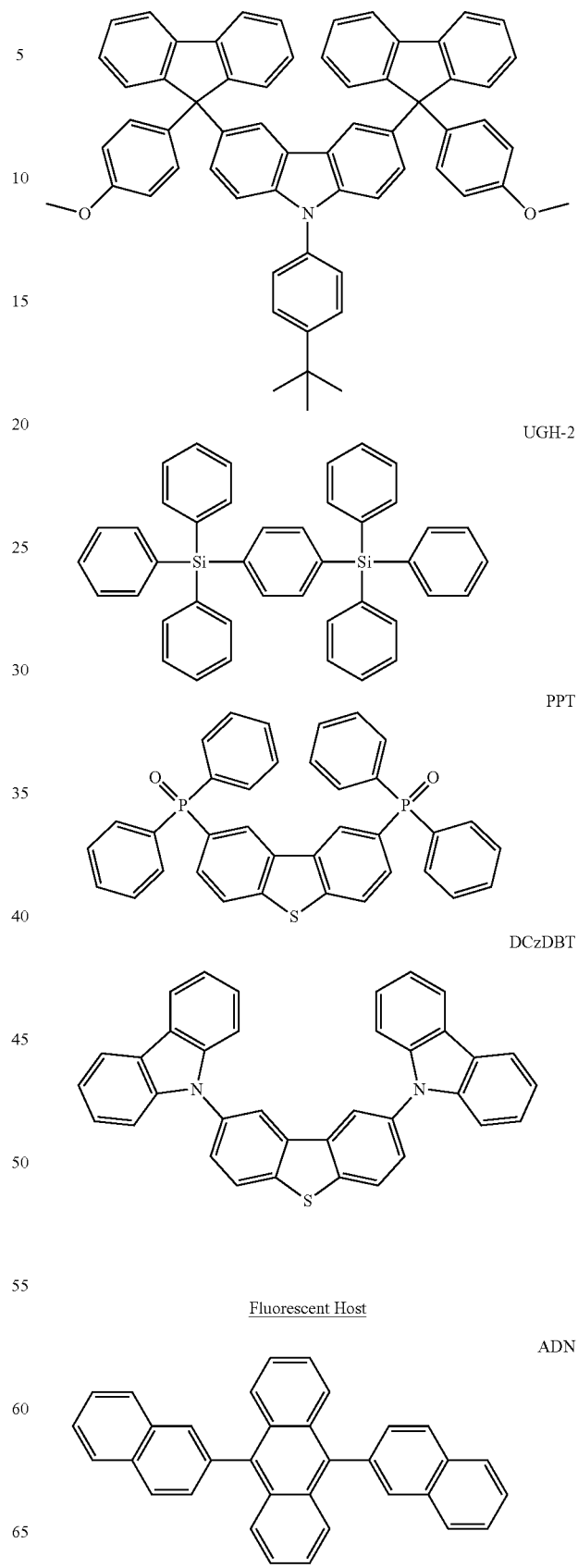
Fluorescent Host TPB3
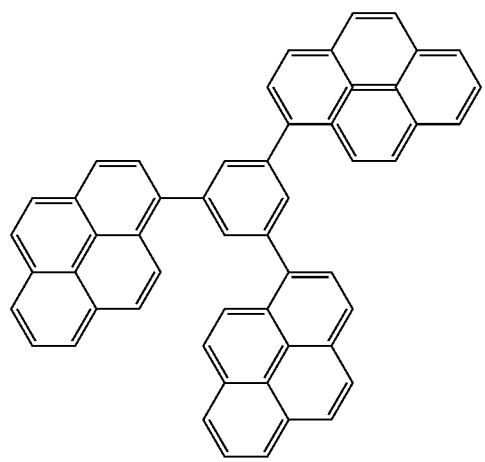
DBP
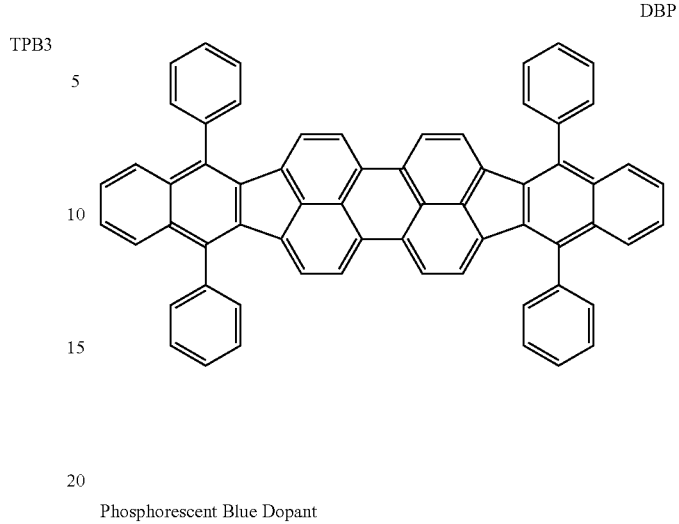
Phosphorescent Blue Dopant
TPBA
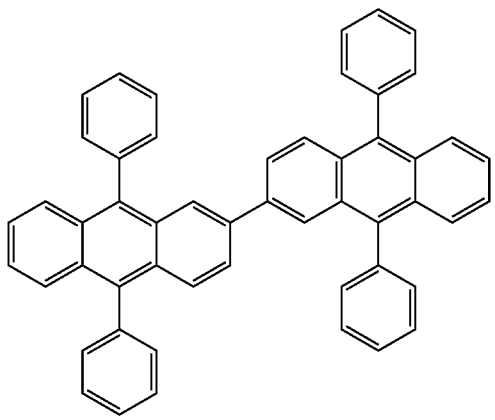
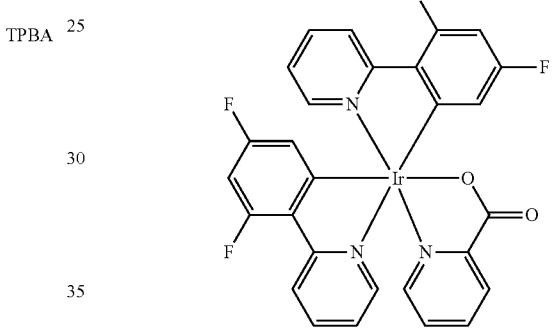
FIrPic
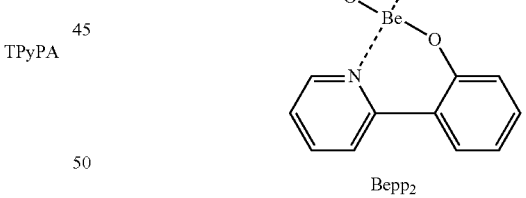
Bepp$_2$
TPyPA
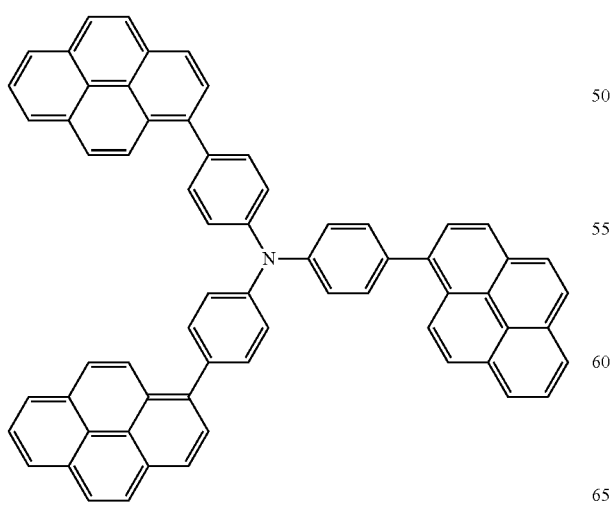
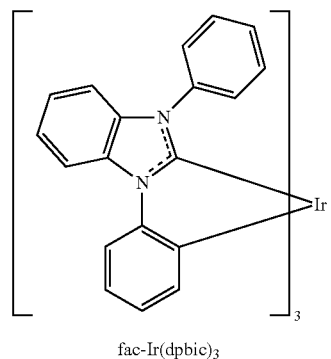
fac-Ir(dpbic)$_3$ Phosphorescent Green Dopant
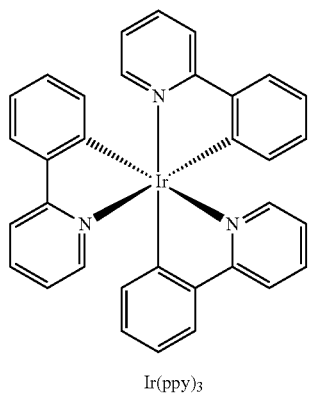
Ir(ppy)₃
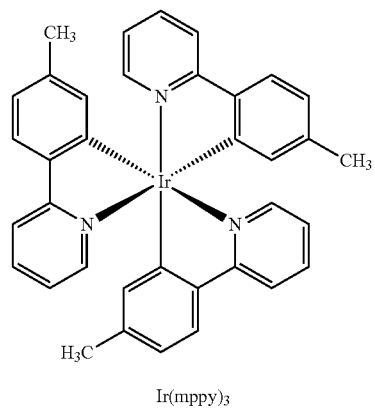
Ir(mppy)₃
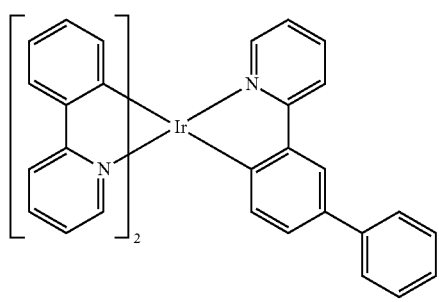
Ir(ppy)₂(m-bppy)
Phosphorescent Red Dopant
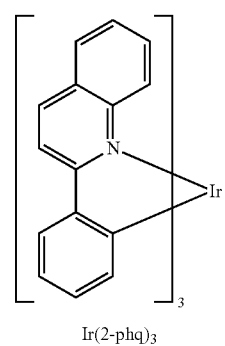
Ir(2-phq)₃
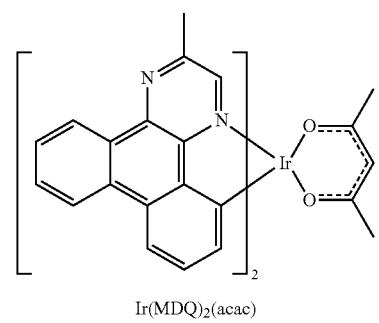
Ir(MDQ)₂(acac)
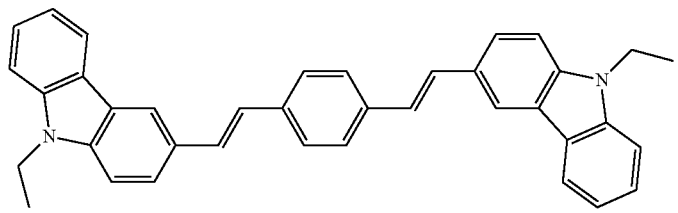
Ir(Mphq)₃
Fluorescent Blue Dopant
BCzVBi -continued
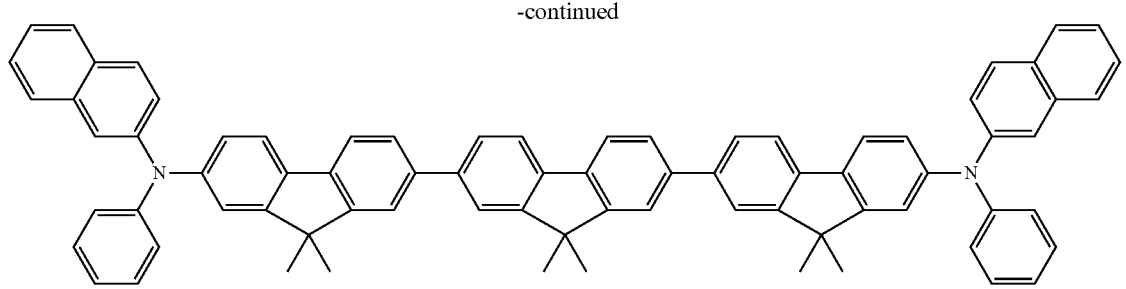
BNP3FL
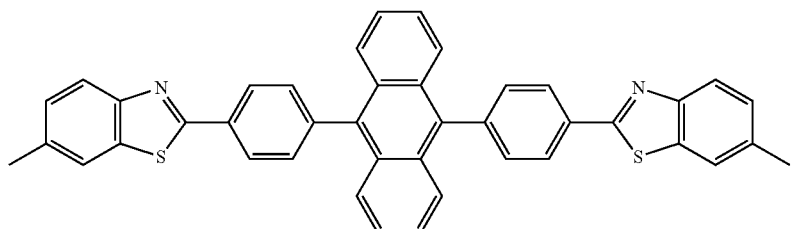
DBzA
Fluorescent Green Dopant
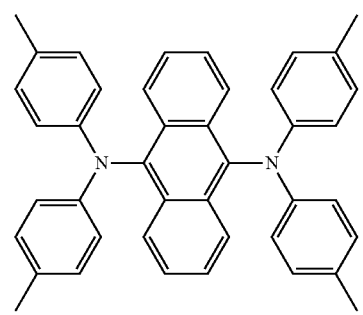
TTPA
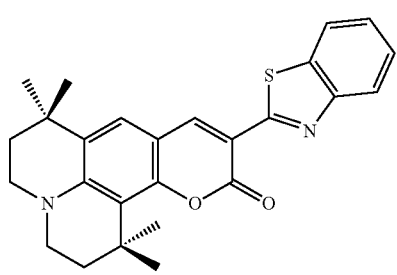
C545T
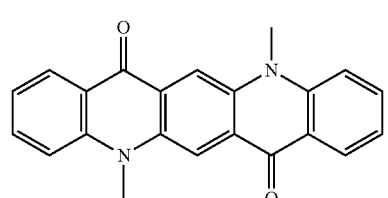
DMQA
Fluorescent Red Dopant
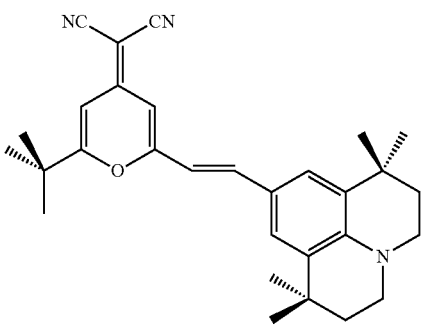
DCJTB
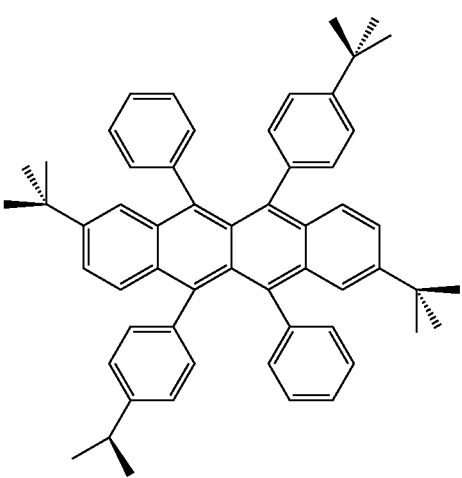
TBRb -continued
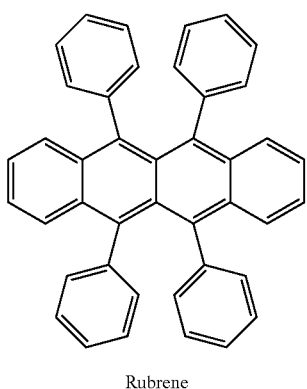
Rubrene
Electron Transport Layer (ETL) Materials
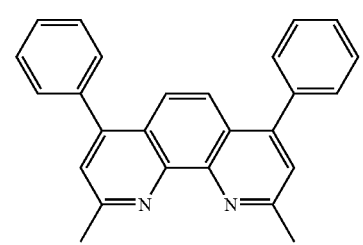
BCP
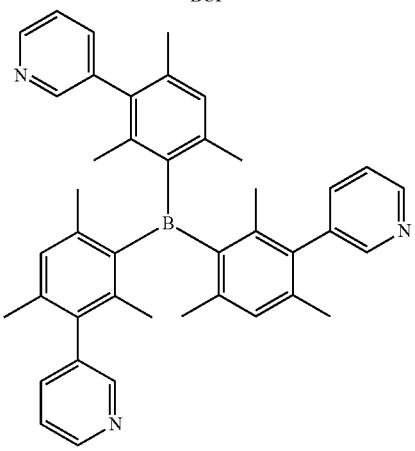
3TPYMB
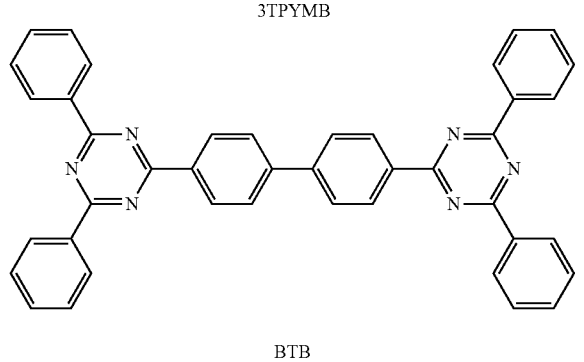
BTB
-continued
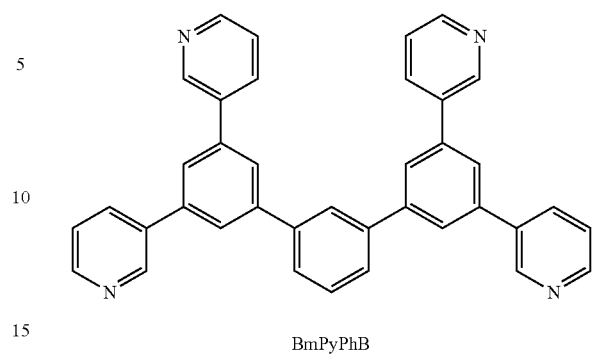
BmPyPhB
Organic Photovoltaic Materials
CuPC
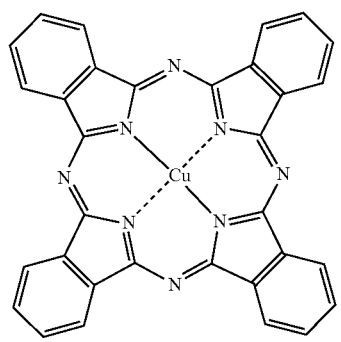
SubPC
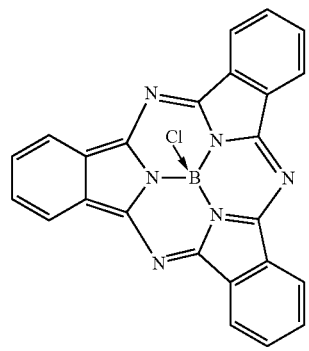
DIP
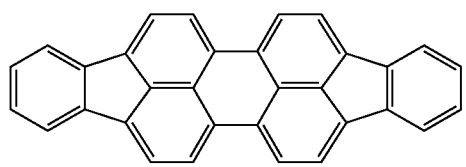
HB194
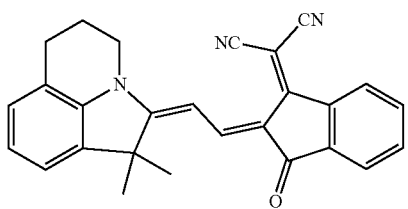

-continued

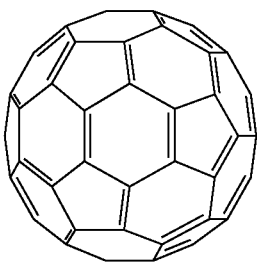

C$_{60}$

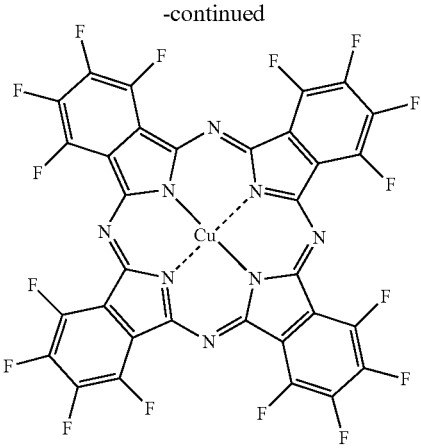

F16CuPC

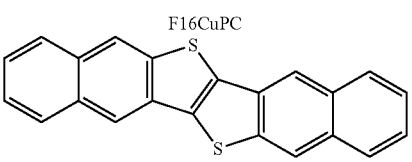

DNTT

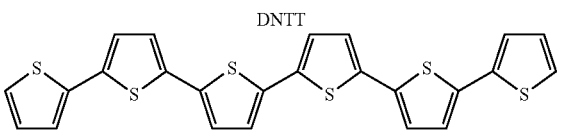

alfa-6T

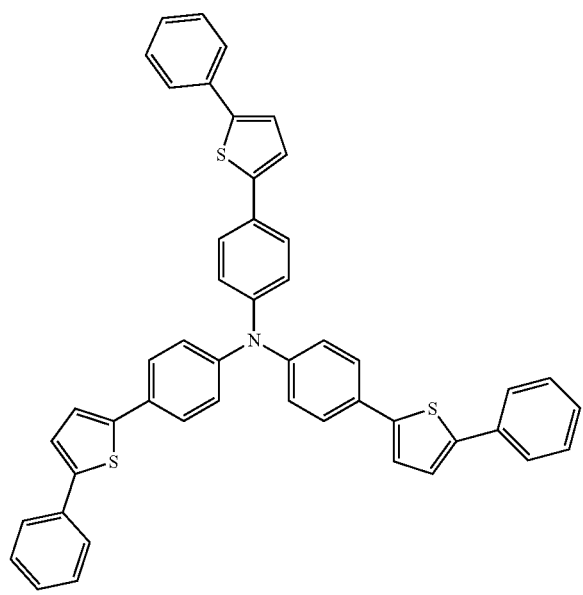

TPTPA

Organic Thin-Film Transistor Materials

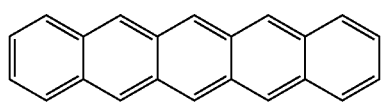

Pentacene

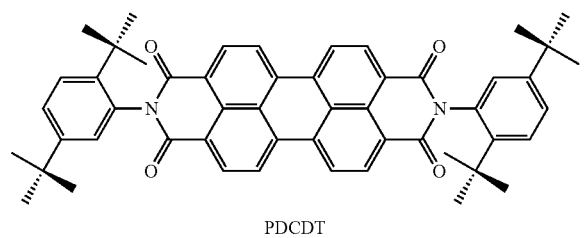

PDCDT

Example 1

Purification for Compound Dipyrazino[2,3-f:2,3-] Quinoxaline-2,3,6,7,10,11-hexacarbonitrile (HAT-CN)

20 g of brown powder of HAT-CN was mixed with 10 g of active carbon and put into quartz boat 202 (see FIG. 2) for sublimation process. Keep the tunnel furnace at a constant temperature (320° C.) for 8 hours. After cooling down to room temperature, scrape out purified HAT-CN from ventral quartz tube to get 8.3 g of white crystal of HAT-CN-Purified, Yield=41.5%.

Example 2

Purification for Compound 9,10-di(naphthalen-2-yl)anthracene (AND)

35 g of yellow powder of ADN was mixed with 20 g of celite and put into quartz boat 302 (see FIG. 3) for sublimation process. Keep the tunnel furnace at a constant temperature (265° C.) for 3 hours. After cooling down to room temperature, scrape out purified AND from ventral quartz tube to get 31 g of light yellow crystal of ADN-Purified, Yield=88.5%.

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high vacuum unit ($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a guest material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device. N,N-Bis(naphthalene-1-yl)-N,N-bis(phenyl)-benzidine (NPB) is most widely used as the hole transporting layer and 4,7-Diphenyl-2,9-bis(4-(1-phenyl-1H-benzo[d]imidazol-2-yl)phenyl)-1,10-phenanthroline (LT-N8001, U.S. Pat. No. 7,754,348) is used as electron transporting material in organic EL device for its high thermal stability and long life-time than BPhen/BCP. 9,10-di(naphthalene-2-yl)anthracene (ADN, U.S. Pat. No. 5,935,721) and 10,10-Dimethyl-12-(4-(pyren-1-yl)phenyl)-1 OH-indeno[1,2-b]triphenylene (PT-302, US20140175384) are used as emitting host and (E)-6-(4-(diphenylamino)styryl)-N,N-diphenyl naphthalen-2-amine (D1) is used as guest. 4,7-Diphenyl-2,9-bis(4-(1-phenyl-1H-benzo[d]imidazol-2-yl)phenyl)-1,10-phenanthroline (LT-N8001, U.S. Pat. No. 7,754,348). The above organic EL materials for producing standard organic EL device in this invention are shown its chemical structure as following:

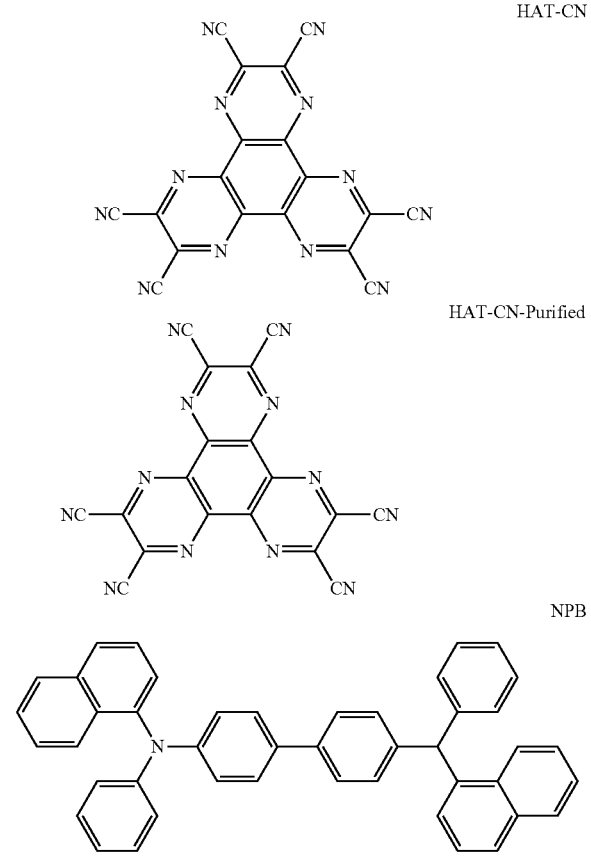

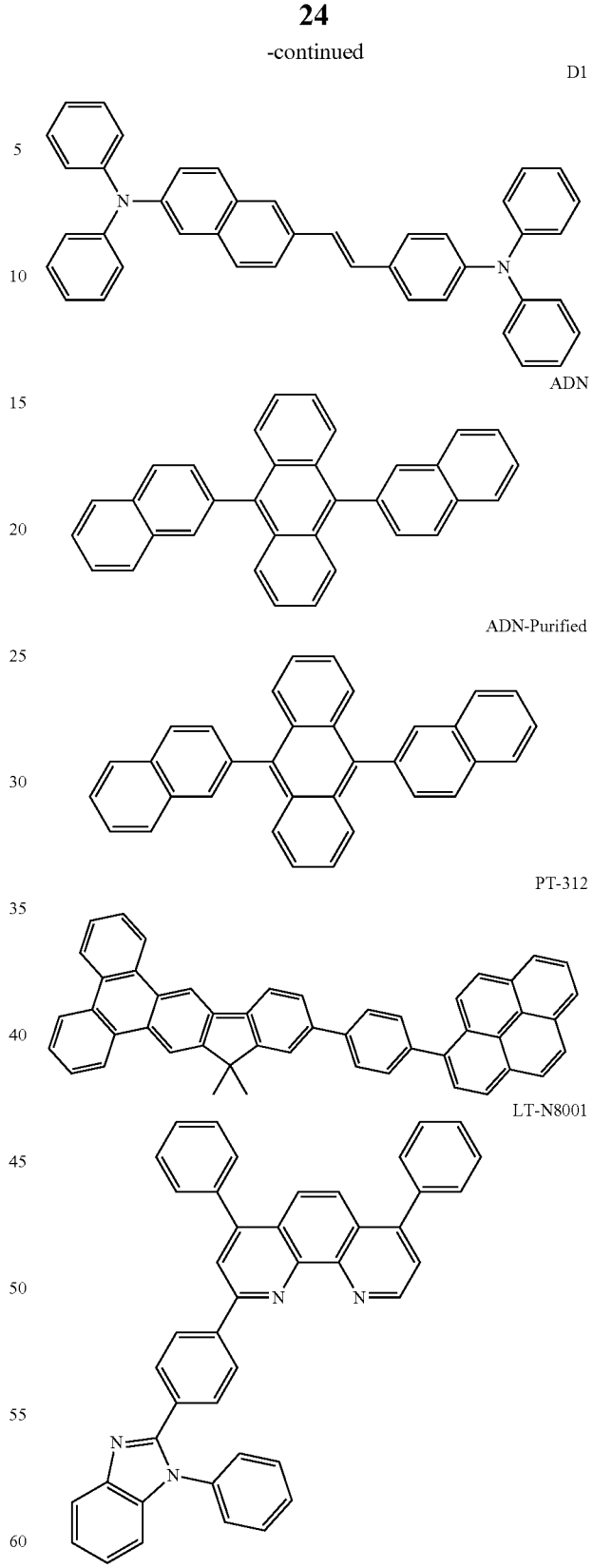

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: Li, LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 3

Using a procedure analogous to the above mentioned general method, fluorescent blue-emitting organic EL device having the following device structure were produced: ITO/HAT-CN (20 nm) or HAT-CN-Purified/NPB (130 nm)/fluorescent blue host (PT-312) doped 5% D1 (35 nm)/LT-N8001 (30 nm)/LiF (0.5 nm)/Al (160 nm). The I-V-B and half-life time of fluorescent blue-emitting OLED device testing report as Table 1, The half-life time is defined that the initial luminance of 1000 cd/m² has dropped to half.

TABLE 1

| Hole injection material | Fluorescent blue host | Voltage (V) | Yield (cd/A) | CIE(y) | Half-lifetime(hour) Initial luminance = 1000(cd/m²) |
|---|---|---|---|---|---|
| HAT-CN | PT-312 | 5.4 | 6.0 | 0.188 | 220 |
| HAT-CN-Purified | PT-312 | 4.8 | 6.3 | 0.188 | 550 |

Example 4

Using a procedure analogous to the above mentioned general method, fluorescent blue-emitting organic EL device having the following device structure were produced: ITO/HAT-CN (20 nm)/NPB (60 nm)/AND or AND-purified doped 5% D1 (35 nm)/LT-N8001 (30 nm)/LiF (0.5 nm)/Al (160 nm). The I-V-B and half-life time of fluorescent blue-emitting OLED device testing report as Table 2, The half-life time is defined that the initial luminance of 1000 cd/m² has dropped to half.

TABLE 2

| Hole injection material | Fluorescent blue host | Voltage (V) | Yield (cd/A) | CIE(y) | Half-lifetime(hour) Initial luminance = 1000(cd/m²) |
|---|---|---|---|---|---|
| HAT-CN | ADN | 7.8 | 2.9 | 0.152 | 150 |
| HAT-CN | AND-Purified | 6.9 | 3.2 | 0.153 | 280 |

In the above preferred embodiments, we show that the material HAT-CN-Purified (From Example 1) and AND-Purified (From Example 2) used as fluorescent blue-emitting organic EL device than comparable example HAT-CN and ADN without using purifying method in the present invention with higher half-life time and practical operation durability. Under the same Luminance (cd/m²), lower driving voltage comparable example HAT-CN and ADN have also been achieved at 1000 cd/m² using the mentioned material purified method from the present invention for blue-emitting organic EL devices.

To sum up, the present invention discloses a purifying method for organic optoelectronic material and their use for organic optoelectronic device are provided. The purifying method for organic optoelectronic material can prolong half-life time, lower driving voltage and power consumption for organic optoelectronic device.

What is claimed is:

1. A purifying method for an organic optoelectronic material comprising a sublimation process to eliminate an impurity from the organic optoelectronic material, wherein the sublimation process is carried out in a quartz tube and the quartz tube comprises:
    (a) a quartz boat placed inside the quartz tube, wherein an adsorbent is mixed with the organic optoelectronic material and the mixed material is put on the quartz boat;
    (b) a quartz boat placed inside the quartz tube, wherein an adsorbent is embedded into a double-layer filter plate covering upon the quartz boat and the organic optoelectronic material is loaded in the quartz boat; or
    (c) a small quartz tube placed inside the quartz tube, wherein a double-layer filter cartridge is placed at each end of the small quartz tube, an adsorbent is embedded into each of the double-layer filter cartridges and the organic optoelectronic material is loaded in the small quartz tube.

2. The purifying method according to claim 1, wherein the organic optoelectronic material comprises an organic electroluminescent material, an organic photovoltaic material or an organic thin-film transistor material.

3. The purifying method according to claim 1, wherein the adsorbent is selected from active carbon, celite, silica gel, zeolite, activated alumina, carbon molecular sieves, molecular sieves and a combination thereof.

4. The purifying method according to claim 1, wherein the impurity is selected from metal ions, halide ions, dying colour, pigments, chromatophores and a combination thereof.

5. The purifying method according to claim 1, the weight ratio of the adsorbent to the organic optoelectronic material is from 1:100 to 100:1.

6. A purifying method for an organic optoelectronic material comprising a deposition process to eliminate an impurity from the organic optoelectronic material, wherein the deposition process is carried out in a deposition machine comprising a heat source and a container placed on the heat source and wherein (a) an adsorbent is mixed with the organic optoelectronic material and the mixed material is put into a container, or (b) an adsorbent is embedded into a double-layer filter plate covering upon a container while the optoelectronic material is loaded in container.

7. The purifying method according to claim 6, wherein the organic optoelectronic material comprises an organic electroluminescent material, an organic photovoltaic material or an organic thin-film transistor material.

8. The purifying method according to claim 6, wherein the adsorbent is selected from active carbon, celite, silica gel, zeolite, activated alumina, carbon molecular sieves, molecular sieves and a combination thereof.

9. The purifying method according to claim 6, wherein the impurity is selected from metal ions, halide ions, dying colour, pigments, chromatophores and a combination thereof.

10. The purifying method according to claim 6, the weight ratio of the adsorbent to the organic optoelectronic material is from 1:100 to 100:1.

* * * * *